United States Patent [19]

Kitajima et al.

[11] Patent Number: 5,135,299
[45] Date of Patent: Aug. 4, 1992

[54] SURGICAL OPERATION MICROSCOPE

[75] Inventors: Nobuaki Kitajima; Kazutoshi Takagi, both of Tokyo, Japan

[73] Assignee: Kabushiki Kaisha Topcon, Tokyo, Japan

[21] Appl. No.: 626,721

[22] Filed: Dec. 14, 1990

[30] Foreign Application Priority Data

Dec. 14, 1989 [JP] Japan .................................. 1-325658

[51] Int. Cl.⁵ .............................................. A61B 3/10
[52] U.S. Cl. ...................................... 351/205; 351/211
[58] Field of Search ............... 351/205, 206, 211, 212, 351/221; 350/507, 513, 514, 515, 516, 526; 128/633; 606/4, 5, 6

[56] References Cited

U.S. PATENT DOCUMENTS

| | | |
|---|---|---|
| 4,533,220 | 8/1985 | Kurita et al. ........................ 350/507 |
| 4,544,243 | 10/1985 | Munnerlyn .......................... 350/514 |
| 4,870,964 | 10/1989 | Bailey, Jr. et al. ................... 351/211 |

FOREIGN PATENT DOCUMENTS

288806 12/1987 Japan .................................. 350/515

Primary Examiner—F. L. Evans
Attorney, Agent, or Firm—Finnegan, Henderson, Farabow, Garrett & Dunner

[57] ABSTRACT

A surgical operation microscope has an observing optical system for observing an eye through an objective lens, and an illuminating optical system for illuminating the eye. The illuminating optical system includes a display element disposed in a position generally conjugate to an observing surface of the eye and adapted to display an image of information required for a surgical operation. The image of information on the display element is projected to the observing surface by an illuminating light source of the illuminating optical system.

13 Claims, 6 Drawing Sheets

SURGICAL OPERATION MICROSCOPE

BACKGROUND OF THE INVENTION

A. Field of the Invention

This invention relates to a surgical operation microscope, and particularly to an operation microscope including an illuminating optical system for illuminating an eye through an objective lens and an observing optical system for observing the eye through the objective lens.

B. Description of the Prior Art

Heretofore, there have been proposed various kinds of surgical operation microscopes. One such example is illustrated in FIG. 11.

Figure 11:
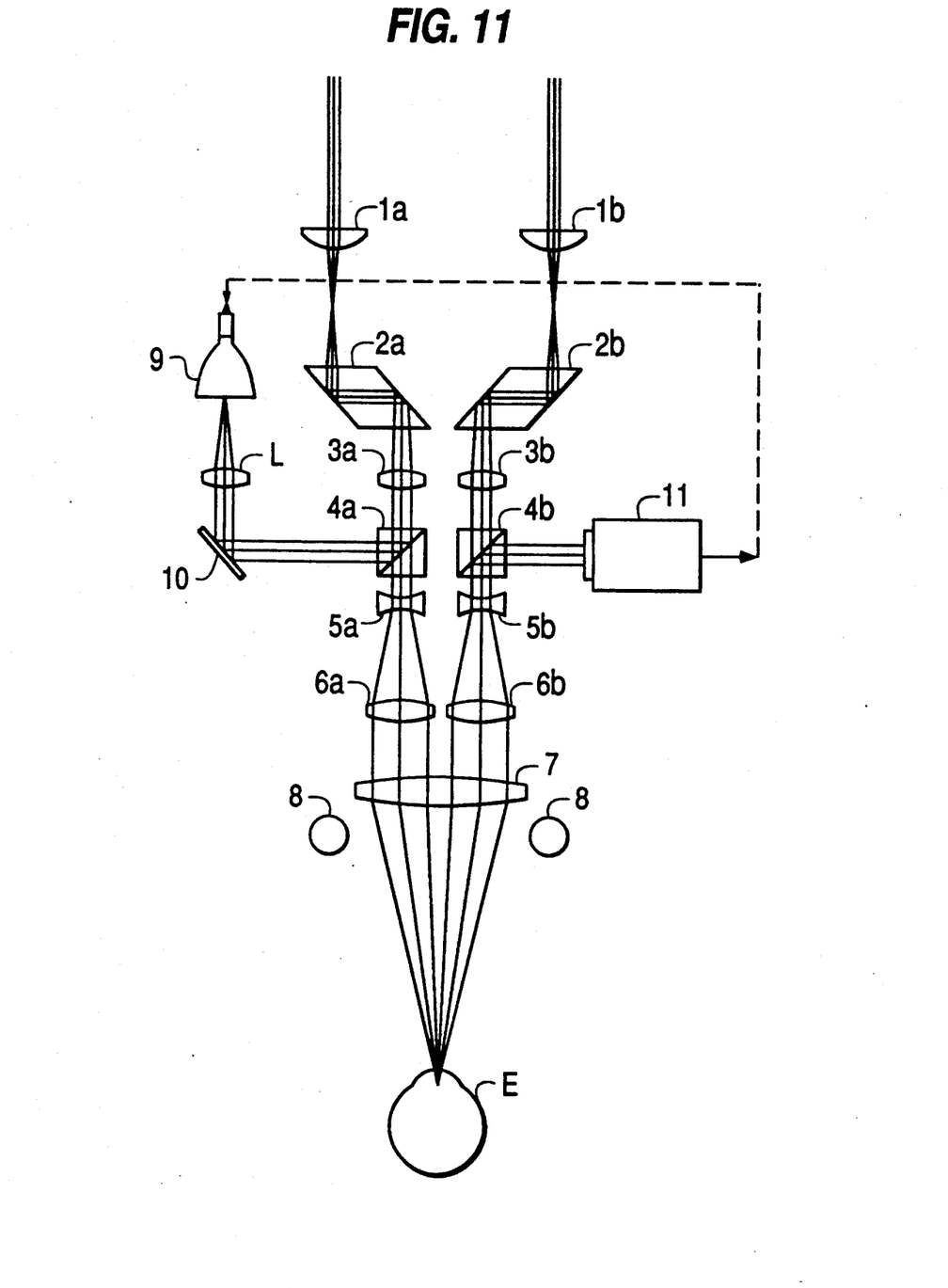
FIG. 11 is a schematic diagram of the optical systems of a conventional surgical operation microscope.

In FIG. 11, the symbolic numerals 1a, 1b denote oculars with which an inspector observes the anterior portion of an eye E, prisms 2a, 2b and imaging lenses 3a, 3b. The symbolic numerals 4a, 4b denote beam splitters. The beam splitter 4a is adapted to guide images of current information to the ocular 1a, and the beam splitter 4b is adapted to split a ray of light reflected by the cornea of the eye E and guide the same both to the ocular lens 1b and to a corneal configuration measuring device 11. The symbolic numerals 5a, 6a, 5b, and 6b denote variable lenses, 7 an objective lens and 8 a ring light source which also serves as a projected target mark. The numeral 9 denotes a display, L a relay lens, and 10 a mirror, respectively.

Data gathered by the corneal configuration measuring device 11 is displayed on the display 9, and the displayed data reaches the ocular 1a through the mirror 10, the beam splitter 4a, the imaging lens 3a and the prism 2a, so that it can be observed.

However, since a surgical operation microscope of the above-mentioned type uses the beam splitters 4a, 4b, light quantity seen through the oculars 1a and 1b is reduced. For that reason, the illuminating light source must be brighter. Under these conditions, it is difficult to protect a patient's eye.

Also, there is another type of a surgical operation microscope which leads a guid images of information on a display to the ocular using a total reflection mirror (for example, disclosed in Japanese utility model early laid-open publication No. Sho 58-62314). While a surgical operation microscope of this type does not require a brighter illuminating light source, a part of the observation field is vignetted by a total reflection mirror.

Another surgical operation microscope has a display element placed directly on an observing surface. In the surgical operation microscope of this type, however the display element must be sterilized because the display element is placed close to a diseased area. This sterilizing operation is troublesome, and the size and the configuration of the display element are limited.

SUMMARY OF THE INVENTION

A object of the present invention is to provide a surgical operation microscope, in which the patient's eye can be protected, a part of the observing field is not vignetted, and no sterilizing operation is required.

Another object of the present invention is to provide a surgical operation microscope, in which a projected image on a display information on an observing surface can always be seen in a proper size irrespective of the magnification.

The present invention includes a display element disposed in a position generally conjugate to an observing surface of an eye and adapted to display images of information required for a surgical operation. The images of information on the display element are projected on the observing surface by an illuminating light source of the illuminating optical system.

A further feature of the present invention is that it includes a transmission type liquid crystal element disposed in a position generally conjugate to an observing surface of an eye to be tested within an optical path of the illuminating optical system and adapted to display an image required for a surgical operation, the image being projected on the observing surface by an illuminating light source of the illuminating optical system, a magnification detecting means for detecting the magnification of the zoom optical system; and a control means for controlling the size of the image displayed on the transmission type liquid crystal element, so that a displayed image projected on the observing surface can be observed in a predetermined size irrespective of the magnification of the zoom optical system.

It is to be understood that both the foregoing general description and the following detailed description are exemplary and explanatory only and are not restrictive of the invention, as claimed.

The accompanying drawings, which are incorporated in and constitute part of this specification, illustrate one embodiment of the invention and together with the description, serve to explain the principles of the invention.

DETAILED DESCRIPTION

The embodiments of the present invention will be described with reference to the drawings.

Figure 1:
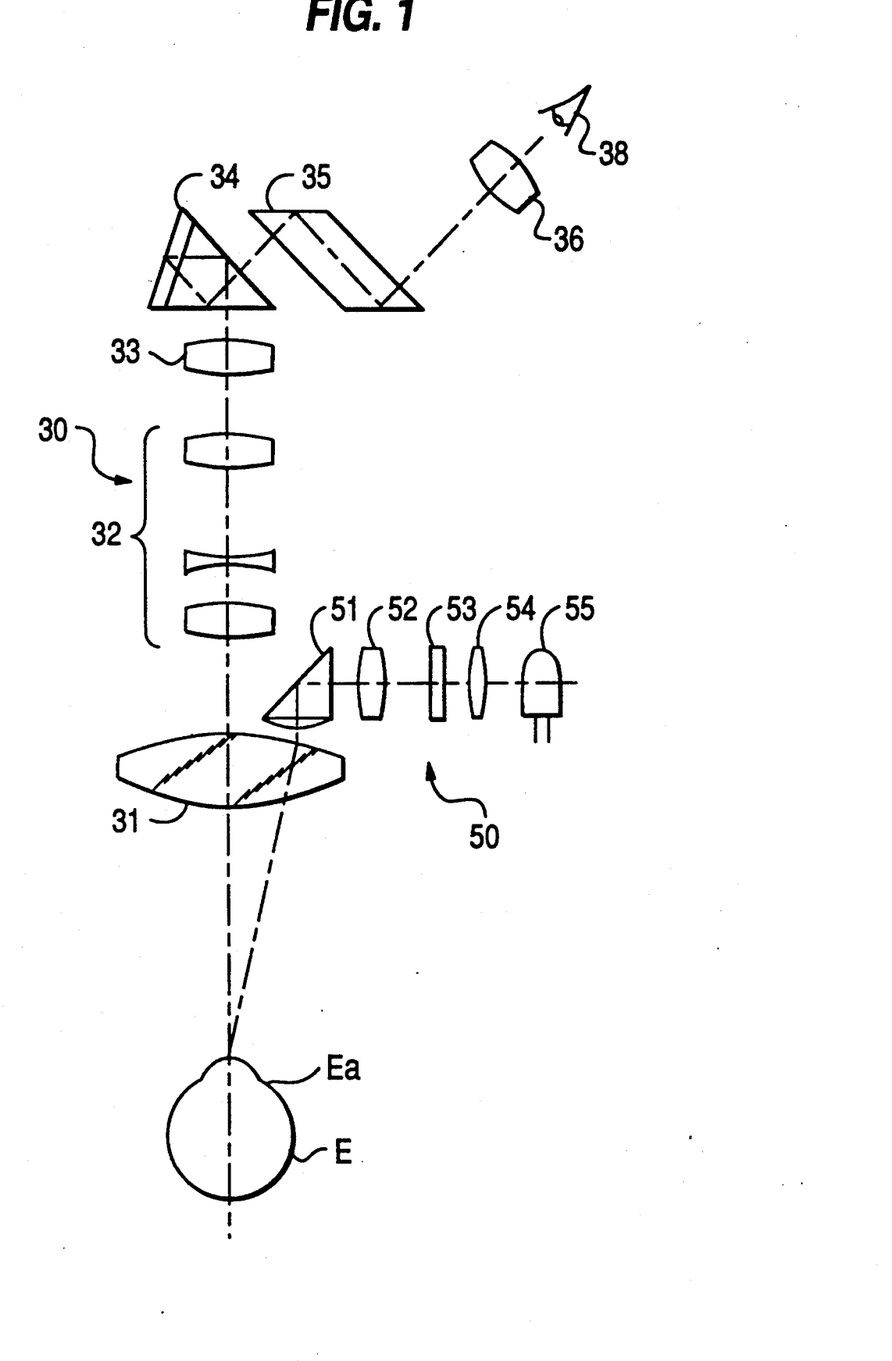
FIG. 1 is a schematic diagram of an optical system of an operation microscope according to the present invention.

FIG. 1 is a diagram schematically showing the arrangement of the optical systems of a surgical operation microscope according to the embodiment of the present invention. In FIG. 1, an observing optical system 30 is designed to observe an eye E through an objective lens 31. Another such observing optical system (not shown)

is provided to make a pair in order to observe the three-dimensionally eye E. The numeral 50 denotes an illuminating optical system for illuminating the eye E through the objective lens 31. This illuminating optical system 50, as shown in FIG. 2, includes an illuminating optical path 50a disposed outside observing optical path 30a of the observing optical system 50, and the eye E is illuminated from this illuminating optical path 50a.

The observing optical system 30 comprises a zoom lens 32, an imaging lens 33, a normal prism 34, a prism 35, and an ocular 36.

The illuminating optical system 50 comprises a lens with a prism 51, a relay lens 52, a display element 53 disposed in a position conjugate to a sclera Ea, a condenser lens 54, and a light source 55.

Figures 2, 3:
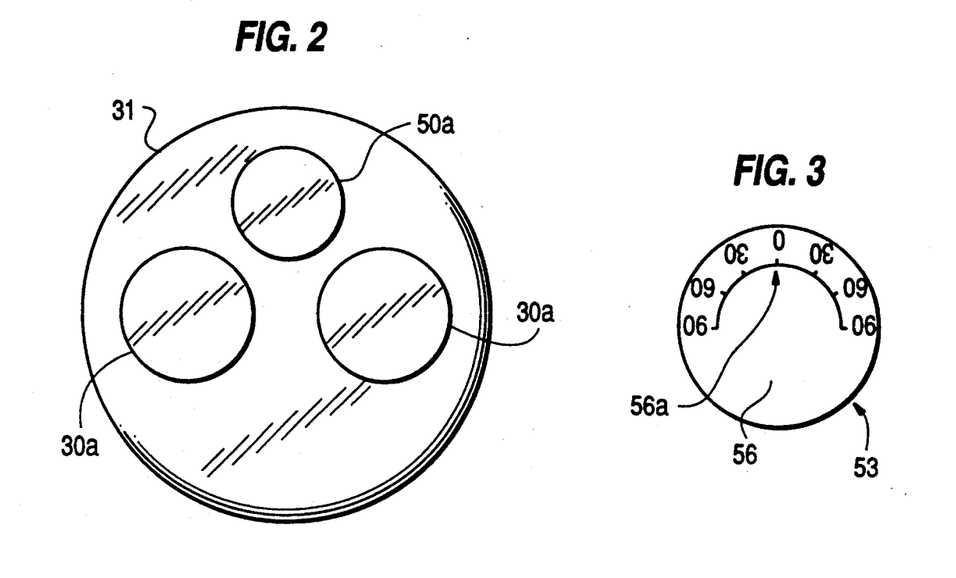
FIG. 2 is an plane view showing optical paths of each optical system through the objective lens of the present invention.
FIG. 3 is a plane view showing a display element of the present invention.

The display element 53 is, for example, a transparent plastic plate 56 attached with an angular scale 56a as shown in FIG. 3.

Hereafter, operation of the surgical operation microscope of the above-mentioned embodiment will be described.

The illuminating light emitted from a light source 55 illuminates the eye E through the illuminating optical path 50a outside the observing optical path 30a through the condenser lens 54, the display element 53, the relay lens 52, the lens 51 with a prism and the objective lens 31. The light beam reflected on the eye E reaches an observing eye 38 through the objective lens 31, the zoom lens 32, the imaging lens 33, the prisms 34, 35, and the ocular 36 allowing the anterior portion of the eye E to be observed.

Figure 4:
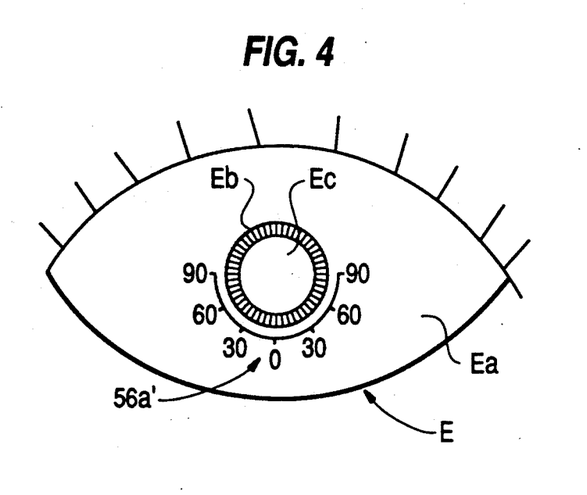
FIG. 4 is an explanatory plane view of illumination of an eye by the present invention.

The display element 53 is in a conjugate relation with the sclera Ea, and the display element 53 is applied with an angle scale 56a as shown in FIG. 3. Accordingly, the angle scale 56a, as shown in FIG. 4, is projected on the sclera Ea in a position serving as an observing surface. And a projected image 56a' of the angle scale 56a can be seen while observing the anterior portion. When, for example, an operation for cataracts is performed, since the cutting angle can be measured while watching the projected image 56a', the operation can be performed very easily. In FIG. 4, Eb denotes iris, and Ec a pupil.

In this way, since it is designed such that the angular scale 56a of the display element 53 is projected on the sclera Ea from the illuminating optical path 50a outside the observing optical path 30a so that the projected image 56a' can be seen together with the anterior portion, the quantity of light illuminating the patient's eye (eye E) can be restrained to a minimum. Moreover, a part of the observing field is not vignetted. Furthermore, since the display element is not placed in a position adjacent to the eye E, a sterilizing operation is not required.

Figure 5:
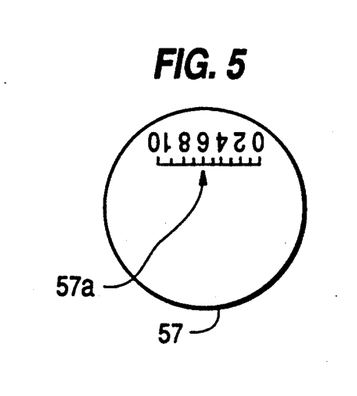
FIG. 5 is a plane view showing another display element of the present invention.

In the above-mentioned embodiment, the display element 53 is provided with the angular scale 56a. As a substitute for this, for example, a display element 57 may, of course, be provided with information such as a dimensional scale 57a required for a surgical operation as shown in FIG. 5.

Also, in the above-mentioned embodiment, the angular scale 56a is projected on the sclera Ea. However, it may be projected on, for example, a piece of sterilized cloth (not shown) or the like covering the adjacent part of the eye E.

Figure 6:
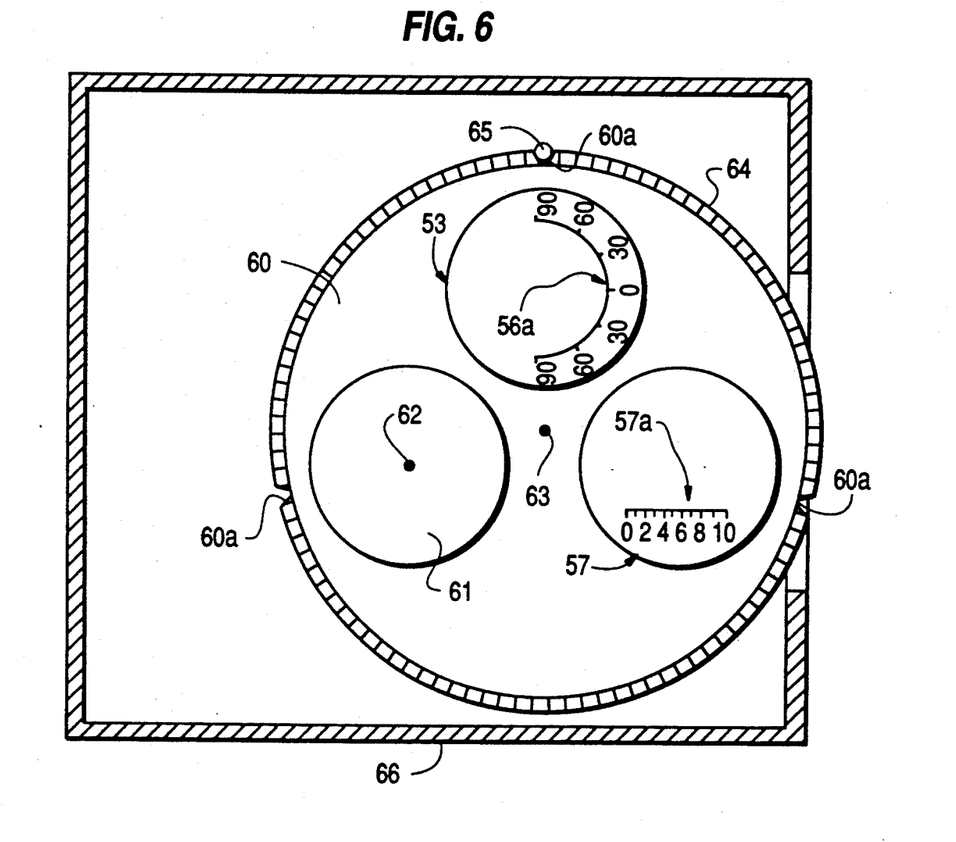
FIG. 6 is an cross-sectional view of a rotational plate of the present invention.

The example shown in FIG. 6 is designed such that the display elements 53, 57 are mounted to a rotational plate 60, so that the angular scale 56a and the dimensional scale 57a can be projected by rotating the rotational plate 60. In FIG. 6, the numeral 61 denotes a through-hole, 62 an optical axis of the rotational plate 60, 64 a roulette formed on the periphery of the rotational plate 60, 65 a click pin engageable with one of the recesses 60a formed on the periphery of the rotational plate 60 to half-fix the rotational plate 60, and 66 a lens-barrel, respectively.

Figure 7:
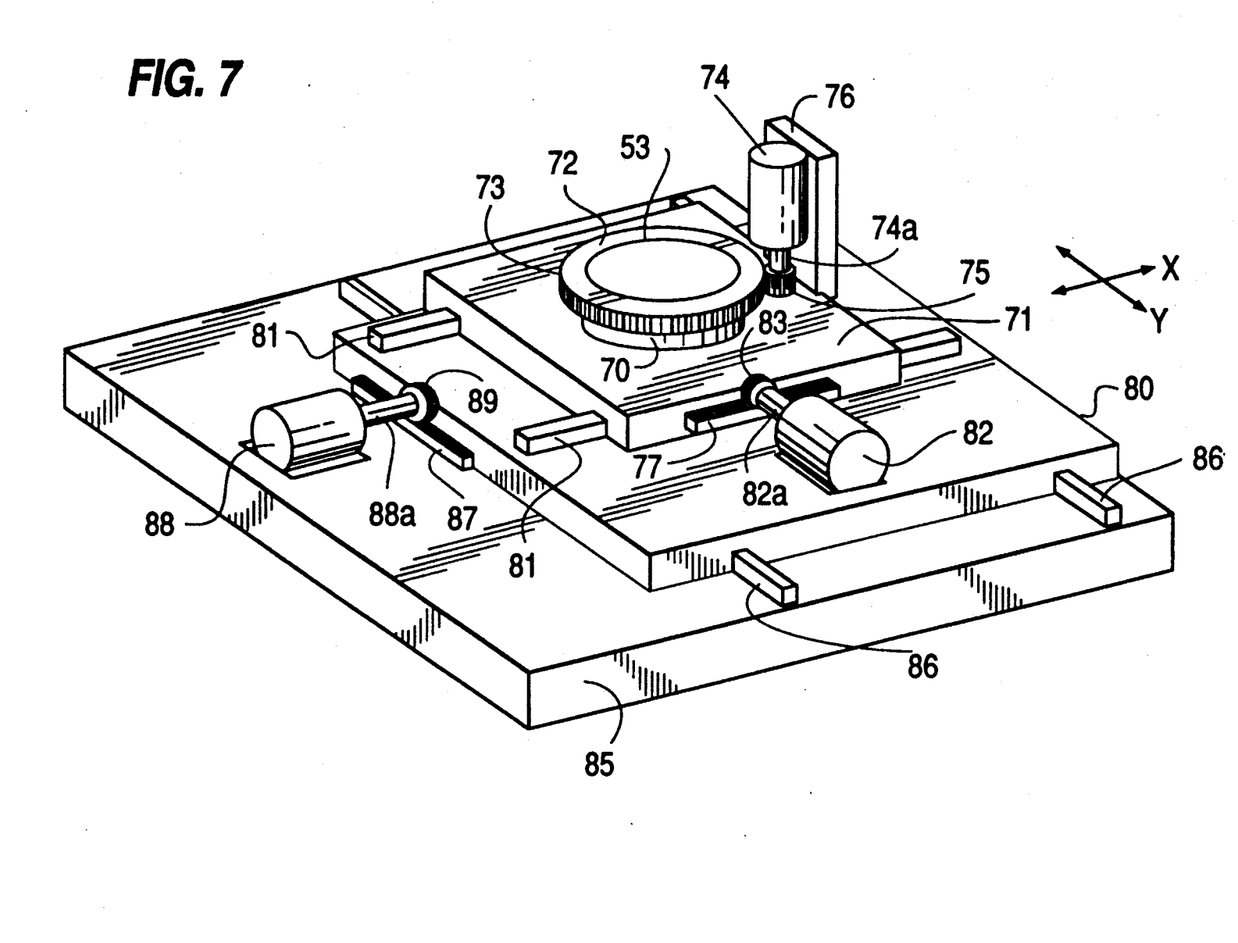
FIG. 7 is a perspective view showing a rotating and moving mechanism of the display element of the present invention.

The example shown in FIG. 7 is designed such that the display element 53 can be rotated and moved in the direction of X and/or Y axes on the plane perpendicular to the optical axis 50a of the illuminating optical system 50.

In FIG. 7, the numeral 70 denotes a cylindrical member which holds the display element 53. This cylindrical member 70 is rotatably mounted to an X-stage 71 and a flange 72 is formed on an upper part of the cylindrical member 70. This flange 72 has a gear 73 formed on a peripheral end face thereof, and the gear 73 is meshed with a pinion 75.

The pinion 75 is mounted on rotating means comprising, for example, a driving shaft 74a of a pulse motor 74, and the cylindrical member 70 is rotated together with the display element 53 by actuation of the motor 74. The motor 74 is installed on a holding member 76 fixed to the X-stage 71.

The X-stage 71 can move in the X-direction along a pair of guide rails 81 disposed on a Y-stage 80. The X-stage 71 has a rack 77 formed on one end portion thereof. A pinion 83 is meshed with the rack 77. The pinion 83 is mounted on moving means comprising, for example, a driving shaft 82a of a pulse motor 82 and the X-stage 71 is moved in the X-direction upon actuation of the pulse motor 82. The pulse motor 82 is fixed to the Y-stage 80.

The Y-stage 80 can move in the Y-direction along a pair of guide rails 86 disposed to a fixed stage 85. The Y-stage 80 has a rack 87 formed on one end portion thereof. A pinion 89 is meshed with the rack 87. The pinion 89 is mounted on moving means comprising, for example, a driving shaft 88a of a pulse motor 88 and the Y-stage 80 is moved in the Y-direction upon actuation of the pulse motor 88. The pulse motor 88 is fixed to the fixed stage 85.

A slit (not shown) extending in the X-direction is formed in the Y-stage 80, while a slit (not shown) extending in the Y-direction is formed in the fixed stage 85, so that even when the X and/or Y-stages 71 and 80 are moved, the illuminating light from the light source 55 is not be blocked.

Figure 8:
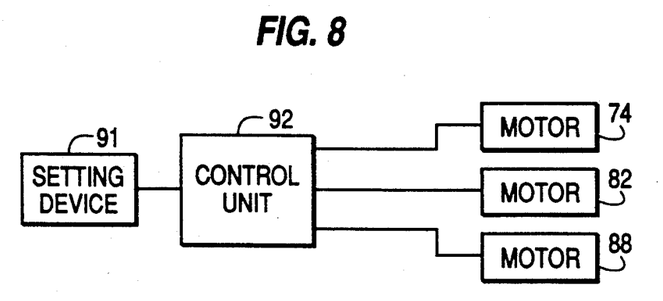
FIG. 8 is a block diagram showing a control system of each pulse motor of the present invention.

FIG. 8 is a block diagram showing the constitution of a control system for controlling the pulse motors 74, 82 and 88. In FIG. 8, the numeral 91 denotes setting means comprising, for example, a setting device for setting an angle of rotation of the display element 53 and a range of movement of the X and/or Y-stages 71 and 80. When an angle of rotation and a range of movement have been set by this setting device 91, a control unit 92 controls the respective pulse motors 74, 82 and 88 to cause the display element 53 to be rotated by the angle which has been set by the setting device 91 and to cause the X and/or Y-stages 71 and 80 to be moved by the desired range. The projected image 56a' of the angular scale 56 shown in FIG. 4 is then rotated and moved bringing it to a proper position.

Figure 9:
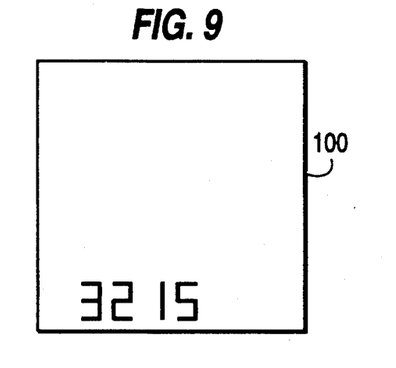
FIG. 9 is a plane view showing a transmission type liquid crystal element of the present invention.

The example shown in FIG. 9 is designed such that the display element comprises a transmission type liquid crystal element 100. This transmission type liquid crystal 100 can display images of various kinds of information required for a surgical operation including information on angle and dimension. Since the images of information displayed on the transmission type liquid crystal element 100 are projected on the observing surface of the sclera Ea or the like, there can be obtained various kinds of information required for a surgical operation without looking away from the ocular 36.

Figure 10:
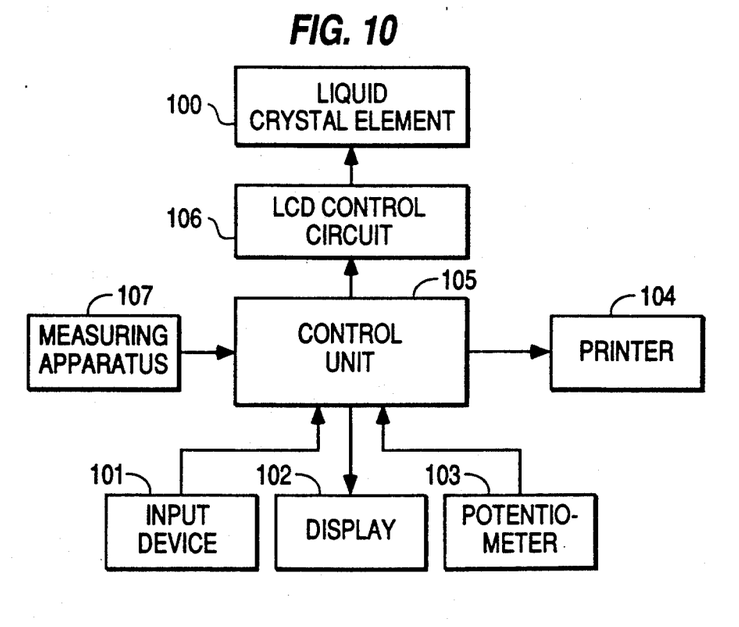
FIG. 10 is a block diagram showing a control system of a transmission type liquid crystal element of the present invention.

FIG. 10 is a block diagram showing the constitution of a control system for controlling the transmission type liquid crystal element 100 in accordance with the magnification of the zoom lens 32. In FIG. 10, the numeral 101 denotes an input device for inputting data required for a surgical operation, 102 a display for displaying an image of current data input into the input device 101 and data, etc. from other measuring apparatuses 107 such as, for example, keratometer, magnification detecting means comprising, for example, a potentiometer 103 for detecting the magnification of the zoom lens 32, a printer 104 and control means comprising, for example, a control unit 105 including a microcomputer, etc., are also provided. This control unit 105 is adapted to control the display 102, the printer 104, etc.

Similarly, the control unit 105 is adapted to calculate the sizes of characters, etc. displayed on the transmission type liquid crystal element 100 based on the magnification detected by the potentiometer 103, so that the projected image of the information displayed on the transmission type liquid crystal element 90 becomes a predetermined size when looked through the ocular 105. The numeral 106 denotes an LCD control circuit for causing the display means to display the characters, etc. in sizes calculated by the control unit 105.

According to this embodiment, when the magnification of the zoom lens 32 is changed, the potentiometer 103 detects the magnification of the zoom lens 32, the control unit 105 calculates the sizes of characters, etc. displayed on the transmission type liquid crystal element 100 based on the magnification detected by the potentiometer 103, so that the projected image of the information displayed on the transmission type liquid crystal element 90 becomes a predetermined size when looked at through the ocular 36.

Accordingly, the size of the projected image looked through the ocular 36 can be constant irrespective of the magnification of the zoom lens 32. Therefore, even if the magnification is desirably changed, there can always be obtained a display of a proper size.

Other embodiments of the invention will be apparent to those skilled in the art from consideration of the specification and the practice of the invention disclosed herein. It is intended that the specification and examples be considered as exemplary only, with a true scope and spirit of the invention being indicated by the following claims and their equivalents.

What is claimed is:

1. A surgical operation microscope comprising:
    an observing optical system having an observing optical path and for observing an eye to be tested through an objective lens; and
    an illuminating optical system having an illuminating optical path and for illuminating said eye through said objective lens from the outside of said observing optical path of said observing optical system, said illuminating optical system including an illuminating light source;
    wherein said illuminating optical system includes a display element having a display surface and disposed in a position generally conjugate to an observing surface of said eye for displaying on said display surface an image of information required for surgical operation; and
    said image of information on said display surface of said display element being projected on said observing surface by said illuminating light source of said illuminating optical system projecting light through said display element.

2. A surgical operation microscope according to claim 1, wherein said display element is disposed in a position conjugate to the sclera of said eye, and the image of information on said display element is projected on the sclera of said eye.

3. A surgical operation microscope according to claim 1, which further includes:
    moving means for moving said display element in the direction of two perpendicular axes in a plane perpendicular to said illuminating optical path of said illuminating optical system; and
    rotating means for rotating said display element in said plane.

4. A surgical operation microscope according to claim 3, which further includes a setting means for setting a range of movement and angle of rotation of said display element.

5. A surgical operation microscope according to claim 1, wherein said display element comprises a transmission type liquid crystal element.

6. A surgical operation microscope according to claim 3, wherein said display element comprises a transmission type liquid crystal element.

7. A surgical operation microscope according to claim 2, further including:
    means for moving said display element in the direction of two perpendicular axes in a plane perpendicular to the optical axis of said illuminating optical system; and
    means for rotating said display element in said plane.

8. A surgical operation microscope according to claim 2, wherein said display element comprises a transmission type liquid crystal element.

9. A surgical operation microscope comprising:
    an observing optical system having a zoom optical system and an observing optical path, said observing optical system for observing an eye through an objective lens;
    an illuminating optical system having an illuminating optical path and for illuminating said eye through said objective lens from the outside of said observing optical path of said observing optical system, said illuminating optical system including an illuminating light source;
    a transmission type liquid crystal element having a display surface and disposed in a position generally conjugate to an observing surface of said eye within an optical path of said illuminating optical system for displaying on said display surface an image of information required for a surgical operation, said image of information being projected on said observing surface by said illuminating light source of said illuminating optical system projecting light through said transmission type liquid crystal element;
    magnification detecting means for detecting a magnification of said zoom optical system; and
    control means for controlling the size of said image of information displayed on said display surface of said transmission type liquid crystal element, so that a displayed image projected on said observing surface can be observed in a predetermined size irrespective of the magnification of said zoom optical system.

10. A surgical operation microscope according to claim 9, wherein said transmission type liquid crystal element is disposed in a position conjugate to the sclera of said eye, and the image of information on said transmission type liquid crystal element is projected to the sclera of said eye.

11. A surgical operation microscope according to claim 9, which further includes:
moving means for moving said transmission type liquid crystal element in the direction of two perpendicular axes in a plane perpendicular to said illuminating optical path of said illuminating optical system; and
rotating means for rotating said display element in said plane.

12. A surgical operation microscope according to claim 11 including a setting means for setting range of movement and an angle of rotation of said transmission type liquid crystal element.

13. A surgical operation microscope according to claim 10, further including:
means for moving said transmission type liquid crystal element in the direction of two perpendicular axes in a plane perpendicular to said illuminating optical path of said illuminating optical system; and
means for rotating said display element in said plane.

* * * * *